United States Patent [19]

Ageland et al.

[11] Patent Number: 5,990,081
[45] Date of Patent: *Nov. 23, 1999

[54] PURIFIED APO A AND APO E COMPOUNDS AND METHODS FOR USING THEM

[75] Inventors: Hans Ageland, Bromma; Lena Romander, Nacka-Strand, both of Sweden

[73] Assignee: Esperion Therapeutics, Inc., Ann Arbor, Mich.

[ * ] Notice: This patent is subject to a terminal disclaimer.

[21] Appl. No.: 09/129,720

[22] Filed: Aug. 5, 1998

Related U.S. Application Data

[63] Continuation of application No. 08/875,125, filed as application No. PCT/SE96/00271, Mar. 1, 1996, Pat. No. 5,834,596.

[30]    Foreign Application Priority Data

Mar. 3, 1995 [SE] Sweden ................................ 9500778

[51] Int. Cl.⁶ .............................. A61K 38/00; C07K 1/00
[52] U.S. Cl. ................................ 514/2; 514/20; 514/21; 530/359; 530/361; 530/402; 530/421; 530/427; 435/69.1; 435/69.6; 424/406
[58] Field of Search .................................. 514/2, 20, 21; 530/359, 361, 402, 421, 427; 435/69.1, 69.6; 424/406

[56]    References Cited

U.S. PATENT DOCUMENTS

| | | | |
|---|---|---|---|
| 4,740,304 | 4/1988 | Tjerneld et al. | 210/639 |
| 5,059,528 | 10/1991 | Bollen et al. | 435/69.4 |
| 5,089,602 | 2/1992 | Isliker et al. | 530/359 |
| 5,128,318 | 7/1992 | Levine et al. | 514/2 |
| 5,834,596 | 11/1998 | Ageland et al. | 530/359 |

FOREIGN PATENT DOCUMENTS

| | | |
|---|---|---|
| 262651 | 4/1988 | European Pat. Off. . |
| 267 703 | 5/1988 | European Pat. Off. . |
| 329 605 A1 | 8/1989 | European Pat. Off. . |
| 0333474 | 9/1989 | European Pat. Off. . |
| 345 155 | 12/1989 | European Pat. Off. . |
| 345 615 | 12/1989 | European Pat. Off. . |
| 0494848 | 7/1992 | European Pat. Off. . |
| 0308336 | 3/1993 | European Pat. Off. . |
| 6228319 | 8/1994 | Japan . |
| 8003198 | 3/1996 | Japan . |
| 88/031666 | 5/1988 | WIPO . |
| WO 90 12879 | 11/1990 | WIPO . |
| WO 91/06655 | 5/1991 | WIPO . |
| 93/12143 | 6/1993 | WIPO . |
| WO 93 25581 | 12/1993 | WIPO . |
| 94/13819 | 6/1994 | WIPO . |
| WO 96/00237 | 1/1996 | WIPO . |
| WO 96/04556 | 2/1996 | WIPO . |
| WO 96/27608 | 9/1996 | WIPO . |

OTHER PUBLICATIONS

F.B. Anspach et al, Removal of Endotoxins by Affinity Sorbents *Journal of Chromatography A*, 711 (1995) 81–92.
S. Minobe et al, Characteristics and Applications of Adsorbents for Pyrogen Removal *Biotechnology and Applied Biochemistry* 10, 143–153 (1988).
H.B. Brewer et al, The Amino Acid Sequence of Human APOA–I, an Apolipoprotein Isolated from High Density Lipoproteins *Biochemical and Biophysical Research Communications*, 80:3 (1978) 623–630.
J.P. Segrest et al, A Molecular Theory of Lipid–Protein Interations in the Plasma Lipoproteins *FEBS Letters*, 38:3 (1974) 247–253.
G. Franceschini et al, A–IMilano Apoprotein: Decreased High Density Lipoprotein Cholesteral Levels with Significant Lipoprotein Modifications and Without Clinical Atherosclerosis in an Italian Family *J Clin. Invest.* 66 (1980) 892–900.
K.H. Weisgraber et al, Apolipoprotein A–IMilano: Detection of Normal A–I in Affected Subjects and Evidence for a Cysteine for Arginine Substitut in the Variant A–I *J. Biological Chemistry*, 258:4 (1983) 2508–2513.
G. Franceschini et al, Apoliporotein A–IMilano: Accelerated Binding and Disassociation from Lipids of a Human Apolipoprotein Variant *J. Biological Chemistry*, 260:30 (1985) 16321–16325.
K. Emancipator et al, In Vitro Inactivation of Bacterial Endotoxin by Human Lipoproteins and Apolipoproteins *Infection and Immunity,*, 60:2 (1992) 596–601.

(List continued on next page.)

*Primary Examiner*—Cecilia J. Tsang
*Assistant Examiner*—Abdel A. Mohamed
*Attorney, Agent, or Firm*—Arnall Golden & Gregory, LLP

[57]    ABSTRACT

A substantially endotoxin-free ApoA or ApoE is produced by recombinant DNA technique, suitably in *E. coli*. Medicaments and methods for treatment of atherosclerosis or cardiovascular diseases employ ApoA or ApoE purified by a process comprising contacting a first aqueous solution comprising ApoA or ApoE and endotoxins with a matrix comprising an immobilized compound with an end group comprising two or three nitrogen atoms bonded to a carbon atom for attaching the endotoxins to the matrix, and subsequently treating the matrix comprising the immobilized compound with a second aqueous solution comprising a surfactant for releasing the ApoA or ApoE while the endotoxins remain attached to the matrix. Alternatively, the ApoA or ApoE is purified by a process comprising contacting the first aqueous solution comprising ApoA or ApoE and endotoxins with an anion-exchange matrix for attaching the ApoA and ApoE to the matrix, treating the anion-exchange matrix with a second aqueous solution comprising a compound comprising two or three nitrogen atoms bonded to a carbon atom for releasing the endotoxins while the ApoA or ApoE remains attached to the matrix, and then releasing the ApoA or ApoE from the matrix.

4 Claims, No Drawings

OTHER PUBLICATIONS

R. Munford et al, Binding of Salmonella Typhimurium Lipopolysaccharides to Rat High–Density Lipoproteins *Infection and Immunity,* 34:3 (1981) 835–843.

T. Karplus et al, A new Method for Reduction of Endotoxin Contamination from Protein Solutions *J. Immuno. Methods,* 105 (1987) 211–220.

C.R. Sirtori et al, Human Apolipoprotein Mutants III: Crystal Structures of the Common Apolipoprotein E Variants: Insights into Functional Mechanisms, *NATO ASI Series,* Springer Verlag, Berlin, vol. II, 73–96 (1993).

Japio Abstract of JP61–96998 (1986).

Abstract of JP1–95798 (1989).

Freudenberg et al (1979) *Nat. Toxins, Proc. Inc. Symp. Anim., Plant Microb. Toxins.,* 6th Edition, pp. 349–354.

Gualandri et al (1985), *Am. J. Hum. Genet.,* vol. 37, pp. 1083–1097.

Ulevitch et al (1981) *J. Clin. Invest.,* vol. 67, pp. 827–837.

Sharma (1986) *Biotechnology and Applied Biochemistry,* vol. 8, pp. 5–22.

Matsumae et al (1990) *Biotechnology and Applied Biochemistry,* vol. 12, pp. 129–140.

Deeb et al (1991) *J. Biological Chemistry,* vol. 266, No. 21, pp. 13654–13660.

Takada et al (1991) *Journal of Lipid Research,* vol. 32, pp. 1275–1280.

Matsunaga et al (1991) *Proc. Natl. Acad. Sci. USA,* vol. 88, pp. 2793–2797.

Weisgraber et al (1980) *J. Clin. Invest.,* vol. 66, pp. 901–907.

Alred et al., "Application of temperature–induced phase partitioning at ambient temperature for enzyme purification," *J Chromatogr A* 659(2):289–98 (1994).

Alred et al., Synthesis of dye conjugates of ethylene oxide–propylene oxide copolymers and application in temperature–induced phase partitioning, *Bioseparation* 2(6):363–73 (1992).

Alred, et al., "Partitioning of ecdysteroids using temperature–induced phase separation," *J. Chromatography* 628:205–214 (1993).

Badimon, et al., "Regression of atherosclerotic lesions by high density lipoprotein plasma fraction in the cholesterol–fed rabbit," *J. Clin Invest.* 85(4):1234–41 (1990).

Berggren, et al., "Effects of salts and the surface hydrophobicity of proteins on partitioning in aqueous two–phase systems containing thermoseparating ethylene oxide–propylene oxide copolymers," *J. Chromatography* 718: 67–79 (1995).

Bradford, et al., "A rapid and sensitive method for the quantitation of microgram quantities of protein utilizing the principle of protein–dye binding," *Anal Biochem* 72:248–54 (1976).

Calebrisi, et al., "Molecular characterization of native and recombinant apolipoprotein A–IMilano dimer. The introduction of an interchain disulfide bridge remarkably alters the physicochemical properties of apolipoprotein A–I," *J Biol Chem.* 269(51): 32168–74 (1994).

Cohn, et al., "Preparation and Properties of Serum and Plasma Proteins. IV. A System for the Separation into Fractions of the Protein and Lipoprotein Components of Biological Tissues and Fluids," *J. Am. Chem. Soc.* 68: 459–475 (1946).

Eisenberg, et al., "A helical hydrophobic moment: a measure of the amphiphilicity of a helix," *Nature* 299: 371–374 (1982).

Fransechini, et al. "Apolipoprotein AIMilano. Disulfide–linked dimers increase high density lipoprotein stability and hinder particle interconversion in carrier plasma," *J Biol Chem.* 265(21):12224–31 (1990).

Fransechini, et al. "High density lipoprotein–3 heterogeneity in subjects with the apo–AIMilano variant," *J. Biol. Chem.* 257(17): 9926–30 (1982).

Harris, et al. "Enzyme purification using temperature–induced phase formation," *Bioseparation.* 2(4): 237–46 (1991).

Index, 11eEd., Merck and Co., Rahway, NJ, pp. 342 and 455 (1989).

Isaachi, et al., "Mature apolipoprotein AI and its precursor proApoAI: influence of the sequence at the 5' end of the gene on the efficiency of expression in *Escherichia coli,*" *Gene* 81(1):129–37 (1989).

Johansson, et al., "Effects of Salts on the Partition of Proteins in Aqueous Polymeric Biphasic Systems," *Acta Chimica Scandivica B* 28: 873–882 (1974).

Lerch, et al., "Isolation and Properties of Apolipoprotein A for Therapeutic Use," *Protides Biol. Fluids* 36: 409–416 (1989).

Medzour, et al. "Anion–exchange fast protein liquid chromatographic characterization and purification of apolipoproteins A–I, A–II, C–I, C–II, C–III0, C–III1, C–III2 and E from human plasma," *J Chromatogr.* 414(1):35–45 (1987).

Moguilevsky, et al., "Production of human recombinant proapolipoprotein A–I in *Escherichia coli:* purification and biochemical characterization," *DNA* 8(6):429–36 (1989).

Nilsson, et al., "Immobilization and purification of enzymes with staphylococcal protein A gene fusion vectors," *EMBO J.* 4(4):1075–80 (1985).

Nitschmann, et al., "Vereinfachtes Verfahen zur Gewinnung von humanem Albumin und—Globulin aus Blutplasma mittels Alkoholfallung," *Helv. Chim. Acta.* 37:866–873 (1954).

Oncley, et al., "The separation of the Antibodies, Isogglutinins, Prothrombin, Plasminogen and β1—Lipoprotein into Subfractions of Human Plasma," *J. Am. Chem. Soc.* 71: 541–550 (1949).

Peitsch, et al., "A purification method for apolipoprotein A–I and A–II," *Anal Biochem.* 178(2):301–5 (1989).

Pigiet, et al., "Thioredoxin–catalyzed refolding of disulfide–containing proteins," *Proc Natl Acad Sci U S A.* 83(20):7643–7 (1986).

Ross, et al., "Rapid chromatographic purification of apolipoproteins A–I and A–II from human plasma," *Anal Biochem* 149(1):166–8 (1985).

Rubenstein, et al., "A new method for the fractionation of human plasma high density lipoprotein," *Can J Biochem.* 55(7):766–8 (1977).

Soma, et al., "Recombinant apolipoprotein A–IMilano dimer inhibits carotid intimal thickening induced by perivascular manipulation in rabbits," *Circ Res.* 76(3): 405–11 (1995).

Walter, et al. Partitioning procedures and techniques: cells, organelles, and membranes, *Methods Enzymol* 228:42–63 (1994).

Weisgraber, et al. "Identification of the disulfide–linked homodimer of apolipoprotein E3 in plasma. Impact on receptor binding activity," *J Biol Chem.* 266(18):12029–34 (1991).

*Dorland's Illustrate Medical Dictionary* (Twenty–fifth Edition) W.B. Saunders–Publisher, 1974.

O'Brien et al, *Circulation,* vol. 98, pp. 519–527, 1998.

PURIFIED APO A AND APO E COMPOUNDS AND METHODS FOR USING THEM

Continuation of prior application Ser. No. 08/875,125 filed Jul. 17, 1997 now U.S. Pat. No. 5,834,596, which is a 371 of PCT/SE96/00271 filed Mar. 1, 1996 and claimed priority of Swedish Application No. SE 9500778-7 filed Mar. 3, 1995.

FIELD OF THE INVENTION

The present invention relates to a substantially endotoxin-free apolipoprotein A (ApoA) or apolipoprotein E (ApoE) and a process for producing the same, by separating the endotoxins from the ApoA or ApoE, or variants or mixtures thereof, by contacting a first aqueous solution containing said ApoA or ApoE with a matrix containing an immobilized compound with an end group comprising two or three nitrogen atoms bonded to a carbon atom, and subsequently treating the matrix containing an immobilized compound with a second aqueous solution containing a surfactant, or by contacting a first aqueous solution containing said ApoA or ApoE with an anion exchange matrix, and subsequently treating the anion-exchange matrix with a second aqueous solution containing a compound comprising two or three nitrogen atoms bonded to a carbon atom. The invention further relates to use of a matrix containing an immobilized compound comprising two or three nitrogen atoms bonded to a carbon atom and a solution containing a surfactant, or an anion-exchange matrix and a solution containing a compound comprising two or three nitrogen atoms bonded to a carbon atom, for removing endotoxins from aqueous solutions containing ApoA or ApoE, or variants or mixtures thereof. The thus produced ApoA or ApoE can be used for the manufacture of a medicament in the treatment of atherosclerosis and cardiovascular diseases, as well as in a method for treatment of atherosclerosis and cardiovascular diseases when administered in a therapeutically effective amount.

BACKGROUND OF THE INVENTION

The dear correlation between elevated levels of serum cholesterol and the development of coronary heart disease (CHD) has been repeatedly confirmed, based on epidemiological and longitudinal studies. The definition, however, of complex mechanisms of cholesterol transport in plasma, has allowed the recognition of a selective function of circulating lipoproteins in determining the risk for CHD.

There are, in fact, four major circulating lipoproteins: chylomicrons (CM), very low density (VLDL), low density (LDL) and high density (HDL) lipoproteins. Of these, HDL is directly involved in the removal of cholesterol from peripheral tissues, carrying it back either to the liver or to other lipoproteins, by a mechanism known as "reverse cholesterol transport" (RCT).

The "protective" role of HDL has been confirmed in a number of studies. Recent-studies directed to the protective mechanism(s) of HDL have been focused on apolipoprotein A-I (ApoA-I), the major component of HDL. High plasma levels of ApoA-I are associated with a reduced risk of CHD and presence of coronary lesions.

Plasma ApoA-I is a single polypeptide chain of 243 amino adds, whose primary sequence is known (Brewer et al. (1978) Biochem. Biophys. Res. Commun. 80: 623–630). ApoA-I is synthesized as a 267 amino acid precursor in the cell. The major structural requirement of the ApoA-I molecule is believed to be the presence of repeat units of 11 or 22 amino acids, presumed to exist in amphipathic helical conformation (Segrest et al. FEBS Lett. (1974) 38: 247–253). This structure allows for the main biological activities of ApoA-I, i.e. lipid binding and lecithin cholesterol acyl transferase (LCAT) activation.

The apolipoprotein A-IMilano (ApoA-IM) is the first described molecular variant of human ApoA-I (Franceschini et al. (1980) J. Clin. Invest. 66: 892–900). It is characterized by the substitution of Arg 173 with Cys 173 (Weisgraber et al. (1983) J. Biol. Chem. 258: 2508–2513). The mutant apolipoprotein is transmitted as an autosomal dominant trait and 8 generations of carriers have been identified (Gualandri et al. (1984) Am. J. Hum. Genet. 37: 1083–1097). The status of a ApoA-IM carrier individual is characterized by a remarkable reduction in HDL-cholesterol level. In spite of this, the affected subjects do not apparently show any increased risk of arterial disease. Indeed, by examination of the genealogical tree it appears that these subjects may be "protected" from atherosclerosis.

The mechanism of the possible protective effect of ApoA-IM in the carriers seems to be linked to a modification in the structure of the mutant apolipoprotein, with the loss of one alpha-helix and an increased exposure of hydrophobic residues (Francheschini et al. (1985) J. Biol. Chem. 260: 1632–1635). The loss of the tight structure of the multiple alpha-helices leads to an increased flexibility of the molecule, which associates more readily with lipids, compared to normal ApoA-I.

Another very specific feature of the ApoA-IM, is its capacity to form dimers with itself and complexes with ApoA-II, in both cases because of the presence of the Cys residue.

To make possible production of sufficient quantities of ApoA-I in general, and more specifically ApoA-IM, use is made of recombinant DNA techniques, e.g in *E. coli*. Thus, recombinant preparation and use of ApoA-IM, monomers as well as dimers, are disclosed in patent specifications WO-A-88/03166 assigned to Farmitalia Carlo Erba (FICE), WO-A-90/12879 assigned to Sirtori et al, as well as WO-A-93/12143 and WO-A-94/13819 both assigned to Pharmacia AB (formerly Kabi Pharmacia AB).

Use of e.g. *E. coli* as medium introduces certain drawbacks. Thus, endotoxins or lipopolysaccharides (LPS) are high molecular complexes associated with the outer membrane (cell wall) of gram-negative bacteria, such as *E. coli*, Proteus and Salmonella. Endotoxins consist of two main parts, a lipid moiety called lipid A which is embedded in the outer membrane and a polysaccharide (O-antigen) which protrudes into the environment. Lipid A is the region which elicit the toxic effect of the endotoxins, a prerequisite being the presence of the entire lipid A moiety. The polysaccharide is made up of a O-specific chain and a core. The O-specific chain projects from the core and is the outermost part of the endotoxin. The core works as a linkage between lipid A and the O-specific chain.

It is known that endotoxins must be released from the bacterial surface to cause toxic effects. This happens when the bacteria multiply, at lysis and during stress. In aqueous solutions, free endotoxins form aggregates, micelles and vesicles, with a molecular weight of about 5 kDa up to $>10^3$ kDa.

It is known from the literature that several proteins form complexes with endotoxins. Particularly strong complexes are formed with HDL and apolipoproteins (Emancipator et al. (1992) Infect. Immun. 60: 596–601). According to Ulevitch et al. (1981) J. Clin. Invest. 67: 827–837, formation of a complex between HDL and endotoxins involve a two step mechanism, as follows:

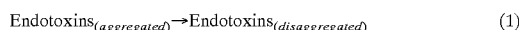

$$\text{Endotoxins}_{(aggregated)} \rightarrow \text{Endotoxins}_{(disaggregated)} \quad (1)$$

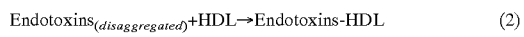

$$\text{Endotoxins}_{(disaggregated)} + \text{HDL} \rightarrow \text{Endotoxins-HDL} \quad (2)$$

This behavior has been confirmed e.g. by Munford et al (1981) Infect. Immun. 34: 835–843. There are indications suggesting that lipid A is the main factor in the complex and that the interaction involves both ionic and hydrophobic forces (Freudenberg et al. (1979) Nat. Toxins, Proc. Int. Symp. Anim., Plant Microb. Toxins., 6th, 349–354).

As already stated above, strong complexes are formed between endotoxins and HDL in general and particularly with apolipoproteins. This mechanism has been used in U.S. Pat. No. 5,128,318 assigned to the Rogosin Institute. U.S. Pat. No. 5,128,318 thus relates to HDL associated apolipoprotein containing reconstituted particles, and use thereof in removing lipid soluble materials, including endotoxins, from cells, body fluids, and the like. More particularly, U.S. Pat. No. 5,128,318 relates to a method for treating a subject for endotoxin-caused toxidty, by administering to the subject a reconstituted particle containing ApoA-I or ApoA-II, with or without cholesterol. Here, naturally, the aim is to create and maintain indefinitely the strongest possible complex, to avoid release of the endotoxins in the subject.

The complexes, strong in themselves, can be further strengthened e.g. by the presence of certain chemical compounds. Thus, deoxycholate is known to disaggregate endotoxins according to formula (1) above (Munford et al., see above and Emancipator et al., see above). The deoxycholate, then increases the binding of endotoxins to HDL according to formula (2). The result is a complex of endotoxins and HDL, which is very difficult to separate.

General methods for reducing or eliminating the effect of endotoxins are known previously. Thus, EP-A-494848 assigned to Pharmacia discloses methods for inhibiting endotoxin induced effects. A first embodiment relates to infusing a medicament containing arginine or arginine derivatives for treatment of an endotoxin induced effect, e.g. fever. A second embodiment relates to a method for removing endotoxins from water or aqueous solutions by filtering the water or aqueous solution through a bed containing immobilized arginine or an arginine derivative. To illustrate the second embodiment, tests were carried out with endotoxins from E. coli on columns containing Arginine SEPHAROSE® from Pharmacia Biotech of Uppsala, Sweden. The interaction is, however, weak and therefore much easier to separate into protein and endotoxins than would be the case with the strong complexes between apolipoproteins and endotoxins.

Anion-exchange chromatography is frequently used in the elimination of endotoxins from solutions containing proteins such as urokinase, interferon, asparaginase and albumin (Sharma (1986) Biotech. Applied Biochem. 8: 5–22). However, the interaction between the proteins and endotoxins is much weaker than the complexes formed between apolipoproteins and endotoxins.

EP-A-333474 to Mitsui Toatsu relates to a process for removing endotoxins from proteins by contacting an endotoxin-contaminated aqueous solution containing the protein with a protein adsorbent, washing the adsorbent with a solution containing an amino compound, and subsequently eluting the protein from the adsorbent. The only exemplified proteins are tissue plasminogen activator (t-PA), human serum albumin and inter-α-trypsin inhibitor. Examples of protein adsorbents are affinity, adsorption, hydrophobic and metal chelate chromatography gels.

Polymyxin B sulfate is an antibiotic polypeptide which has the ability to prevent the toxic effects of endotoxin by interaction with the lipid A moiety. Karplus and coworkers (Karplus et al. (1987) J. Immuno. Methods 105: 211–220) have used this knowledge for adsorbing endotoxins on Polymyxin SEPHAROSE® 4B, sold by Pharmacia AB of Uppsala, Sweden. Polymyxin is, however, in itself biologically active and therefore not suitable for removing endotoxin from solutions for intravenous injection (H. Matsumae et al. (1990) Biotechn. Biochem. 12: 129–140).

PROSEP® Remtox sold by Bioprocessing Ltd. of Great Britain, is a matrix prepared for specific removal of endotoxins from low and high molecular weight substances, such as antibiotics, vitamins, enzymes, antibodies and blood products. The gel consists of a low molecular weight, non-protein, non-carbohydrate synthetic ligand.

Charged filters are capable of removing endotoxins and other negatively charged molecules from different solutions. For example, Pall of United Kingdom offers POSIDYNE™ filters, consisting of a hydrophilic nylon 66 filter medium containing quaternary ammonium groups throughout the membrane structure. The retention capacity of the filter is independent of the temperature and is optimal at a pH of 5–8 and at a low flow rate.

There are presently several methods known for reducing or eliminating the influence of endotoxins in protein solutions generally. There is, however, no existing method to overcome the strong interaction between endotoxins and ApoA or ApoE. The present invention is intended to solve this problem.

DETAILED DESCRIPTION OF THE INVENTION

An object of the present invention is to provide an efficient purifying process for producing ApoA or ApoE with a very low content of endotoxins.

Another object of the present invention is to provide an efficient process, where the activity of the ApoA or ApoE is essentially retained.

A further object of the present invention is a process providing a high yield of ApoA or ApoE, i.e. a process with a minimal loss of product.

The objects above are met by the present invention, which relates to a process for separating endotoxins from apolipoprotein A (ApoA) or apolipoprotein E (ApoE), or variants or mixtures thereof, by contacting a first aqueous solution containing said ApoA or ApoE with a matrix containing an immobilized compound with an end group comprising two or three nitrogen atoms bonded to a carbon atom, and subsequently treating the matrix containing an immobilized compound with a second aqueous solution containing a surfactant, or by contacting a first aqueous solution containing said ApoA or ApoE with an anion-exchange matrix, and subsequently treating the anion-exchange matrix with a second aqueous solution containing a compound comprising two or three nitrogen atoms bonded to a carbon atom.

The inventors of the present invention have surprisingly found that matrices containing e.g. immobilized arginine, guanidine or histidine, can be used to strongly attach the endotoxins, and thereby the ApoA or ApoE, to the matrix. By subsequently eluting with a-surfactant-containing solution, the ApoA or ApoE molecules can be released, while the endotoxins remain attached to the matrix. It is also possible to strongly attach the ApoA or ApoE and thereby the endotoxins to an anion-exchange matrix. By subsequently eluting with a solution containing e.g. urea or arginine, or salts of guanidine or histidine, the endotoxins can be released, while the ApoA or ApoE molecules remain attached to the matrix. Finally, the ApoA or ApoE molecules can be released from the matrix by increasing the ionic strength.

The selection of conditions under which to perform the present process will be governed by a desire to reach as low concentration of the endotoxins as possible, while at the same time obtain an acceptable recovery of the ApoA or ApoE.

With the present process it is possible to produce ApoA or ApoB which are substantially endotoxin-free. In the present invention, substantially endotoxin-free means a concentration below about 1 EU/mg of ApoA or ApoE. Specifically, it is possible to produce substantially endotoxin-free ApoA or ApoE which have been produced-by recombinant DNA technique, more specifically in gram-negative bacteria, and even more specifically in $E.$ $coli$ With the present process it is possible to produce ApoA or ApoE with a low content of endotoxin in combination with a protein recovery of at least 70%, suitably at least 80%, preferably at least 90% and more preferably at least 95%.

The present invention also relates to use of a matrix containing an immobilized compound with an end group comprising two or three nitrogen atoms bonded to a carbon atom and a solution containing a surfactant, or an anion-exchange matrix and a solution containing a compound comprising two or three nitrogen atoms bonded to a carbon atom, for removing endotoxins from aqueous solutions containing ApoA or ApoE, or variants or mixtures thereof.

The present invention further relates to use of ApoA or ApoE produced according to the inventive process for the manufacture of a medicament comprising the ApoA or ApoE in the treatment of atherosderosis and cardiovascular diseases.

The present invention further relates to a method for treatment of atherosclerosis and cardiovascular diseases, by administering ApoA or ApoE produced according ito the inventive process in a therapeutically effective amount.

In a first embodiment, an aqueous solution containing ApoA or ApoE is loaded onto a matrix with immobilized ligands with an end group comprising two or three nitrogen atoms bonded to a carbon atom. Subsequently, the complex of ApoA or ApoE and endotoxins is separated by eluting with an aqueous solution containing a surfactant, whereby the ApoA or ApoE is released while the endotoxins remain attached to the ligands. Finally, the matrix is regenerated by washing with one or more liquids containing various combinations of e.g. NaOH, $C_2C_5OH$, HAc and NaAc.

Examples of end groups that can be used in the present invention are those containing a guanidyl group, e.g. arginine and guanidine, or a heterocyclic group, e.g. histidine. The end groups are suitably non-heterocyclic, preferably containing a guanidyl group rendering the end groups strong bases. The end group containing a guanidyl group is more preferably arginine or guanidine, most preferably arginine. The end groups can be bonded directlyto the matrix. More commonly, however, the end group is bonded to the matrix through a spacer, which can be inert or exhibit additional binding capacity. Spacers well suited for the present process can be found e.g. in Arginine bonded to SEPHAROSE® and Histidine bonded to MINILEAK®.

In a second embodiment, an aqueous solution containing ApoA or ApoE is loaded onto an anion-exchange matrix. Subsequently, the complexes of ApoA or ApoE and endotoxins are separated by eluting with an aqueous solution containing a compound comprising two or three nitrogen atoms bonded to a carbon atom. In this way the endotoxins are released while the ApoA or ApoE remain attached to the ligands. Suitable examples of the nitrogen-containing compounds are urea, arginine and guanidine hydrochloride. Finally, the ApoA or ApoE are released from the matrix by increasing the ionic strength, suitably to about 0.5 up to about 2 M, preferably by addition of NaCl.

Conventionally, in processes for purifying proteins the concentrations of e.g. urea and guanidine hydrochloride are kept at a minimum to avoid irreversible denaturation of the protein at issue. Surprisingly, the inventors have found that a higher than conventional concentration of the nitrogen-containing compound is advantageous when carrying out the present invention, since it facilitates the uncovering of the strong complex between endotoxins and ApoA. Thus, the concentration of urea should be in the range of from about 0.75 M up to saturation at the prevailing temperature, suitably in the range of from 2.5 M up to 8 M, preferably from 4.5 up to 7.5 M. It lies within the competence of the person skilled in the art to select the corresponding concentrations for e.g. guanidine hydrochloride and arginine.

In a third embodiment, the first and second embodiments are combined so as to give a product with a very low level of endotoxin. Thus, the aqueous solution containing ApoA or ApoE can be loaded onto an anion-exchange step whereafter the endotoxins are released by eluting with a compound comprising two or three nitrogen atoms bonded to a carbon atom. The ApoA or ApoE with a reduced concentration of endotoxins, are released from the anion-exchange matrix, and, optionally after one or more intermediate process steps such as a desalting step, the resulting ApoA or ApoE is loaded onto a matrix with immobilized compounds with end groups comprising two or three nitrogen atoms bonded to a carbon atom. Finally, the ApoA or ApoE can be released in a very pure form. The reversed sequence, i.e. a first step with a matrix containing immobilized ligands, and a second step with an anion-exchange matrix, can also be used to advantage in the present invention.

The matrices of the present invention can be soluble or insoluble in various common solvents, e.g. organic polymers soluble or insoluble in water with or without ethanol. Matrices also include e.g. filters to which ligands comprising two or three nitrogen atoms bonded to a carbon atom have been coupled.

The immobilized compounds with an end group comprising two or three nitrogen atoms bonded to a carbon atom can be supported on any inorganic or organic matrix. Thus, the matrix can be selected from various strongly hydrophilic matrices e.g. agarose matrices such as a wide variety of SEPHAROSE® matrices sold by Pharmacia Biotech of Uppsala, Sweden, organic polymer matrices such as TSK-gels sold by Tosoh Corp. of Tokyo, Japan, or highly porous organic polymer matrices sold by Per Septive Bio-systems of Boston, USA. The matrix is preferably an agarose matrix. Suitable agarose matrices in the present invention are, apart from SEPHAROSE®, MINILEAK® sold by Kem-En-Tec A/S of Copenhagen, Denmark and Bio-Gel A sold by Bio-Rad, of Brussels, Belgium. Preferably, the matrix is cross-linked allowing for a fast flow (FF) and thereby high production capacity.

Anion-exchange matrices useful in a process according to the second embodiment, are e.g. agarose matrices such as DEAE SEPHAROSE® and Q SEPHAROSE® matrices sold by Pharmacia Biotech of Uppsala, Sweden. Further examples of anion-exchange matrices that can be used in the present process are Super Q-650 and Fractogel EMD DEAE-650 sold by Toso Haas of Tokyo, Japan, and Hyper D sold by Biosepra S.A. of France. The anionexchange matrix is suitably an agarose matrix. Preferably, the anion-exchange matrix is cross-linked allowing for a fast flow (FF) and thereby high production capacity.

The present invention is advantageously used for removing endotoxins from any apolipoprotein A (ApoA) or Apolipoprotein E (ApoE), or variants or mixtures thereof. The present invention is especially suitable when the ApoA or ApoE are produced by a recombinant DNA technique in gram-negative bacteria, and in particular when they are produced in E. coil. In the present invention, the terms ApoA and ApoE include any preform or fragment, or any truncated, extended or mutated form, or any mixture of any of these forms or fragments. Preform relates e.g. to the 249 amino acid Met form of ApoA-I as disclosed in WO-A-88/-03166 assigned to Sirtori et al. Other preforms are the proapolipoprotein A-Is disclosed in U.S. Pat. No. 5,059,528 to UCB as well as EP-A-308336, JP 216988/1984 and JP 252048/1987 all to Mitsubishi Chem. Ind. Fragment relates to a part of ApoA or ApoE containing at least one alpha helix, e.g. as disclosed in WO-A-93/25581 assigned to Innogenetics S.A. of Belgium. Truncated and extended forms relate to ApoA and ApoE molecules where one or more amino acid is missing or has been added, respectively, at the N and/or C terminal ends of the molecules. Suitably, from two up to eight amino acids are missing or have been added, preferably from three up to six amino acids. Mutated forms relate to ApoA and ApoE molecules where one or more amino acid has been substituted by another amino acid, e.g. ApoA-IM as disclosed in WO-A-93/12143 and WO-A-94/13819. Other mutated forms are ApoA-ISeattle (Deeb et al (1991) J. Bio. Chem. 266: 13654–13660), ApoA-IYame (Takada et al (1991) J. Lipid Res. 32: 1275 ff) and a yet unnamed mutated form of ApoA-I (Matsunaga et al (1991) Proc. Natl. Acad. Sci. USA 88: 2793–2797).

Human ApoE and variants thereof, are disclosed in "Human Apolipoprotein Mutants III", ed. by C. R. Sirtori et al (1993) Nato ASI Series, Springer Verlag, Berlin, II 73: 81–96.

The present invention can be used to advantage for removing endotoxins from ApoA as well as ApoE. In the following description, however, use will be made of ApoA to further describe the present invention.

Known ApoAs are e.g. ApoA-I, ApoA-II and ApoA-IV. In the present invention, suitably, the ApoA is ApoA-I, or variants or mixtures thereof. Natural ApoA-I is a single polypeptide chain, composed of 243 amino acids. More suitably, the ApoA is a mutated form of ApoA-I where at least one Cys residue has been substituted for a Arg residue making formation of disulfide-linked dimer possible. In the amino add sequence of natural human ApoA-I, Arg residues are located at positions 10,27,61,83,116,123,131,149,151, 153,160,171,173,177,188 and 215. Of these, substitutions are preferred at one or more of positions 160,171, 173,177 and 188, i.e. at positions within the same alpha helix. More preferably, the Arg residue is substituted at positions 171 and/or 173.

Human apolipoprotein A-IMilano (ApoA-IM) is a naturally occurring mutated form of normal ApoA-I (Weisgraber et al. (1980) J. Clin. Invest. 66: 901–907). In ApoA-IM, one residue of the amino acid arginine (Arg 173) has been replaced by a residue of the amino acid cysteine (Cys 173). Since ApoA-IM contains one cysteine residue per polypeptide chain, it may exist as a monomer or as a disulfide-linked dimer. The molecular weight of the monomer is about 28,000 Da and for the dimer about 56,000 Da. These two forms are chemically interchangeable, and the term-ApoA-IM does not, in the present context, discriminate between the two forms.

The initial concentration of endotoxin in the aqueous solutions containing ApoA, may be more than $10^6$, more than $10^7$, and even more than $10^8$ EU/mg of protein. The final concentration of endotoxin can be reduced to below about 100 EU/mg, by applying the present invention to the aqueous solutions containing ApoA. Suitably, the final concentration of endotoxin is reduced to below about 10 EU/mg, and preferably to below about 1 EU/mg, rendering the Apo A substantially endotoxin-free.

To reach low levels of endotoxin in the aqueous solutions containing ApoA, it may be necessary to recirculate the solution so that it is contacted with the matrix at least twice. It is of course also possible to use the same or different matrices in at least two consecutive steps, to reach a sufficiently low level of endotoxins. In any of these ways, it is possible to reduce the initial concentration of endotoxins by at least $10^4$, suitably by at least $10^5$, and preferably by at least $10^6$ in the process.

The mitrix is normally equilibrated with a first buffer before the sample containing ApoA is loaded onto the matrix. After loading, the matrix is treated with a second buffer to elute the essentially endotoxin-free ApoA from the matrix.

In a preferred embodiment, the first aqueous solution containing ApoA further contains a surfactant. The surfactant is added in order to at least partially disaggregate the complexes between the endotoxins and ApoA before contacting said first aqueous solution with the matrix. Thus, by maintaining the first aqueous solution containing a surfactant for at least 5 min before contacting said first aqueous solution with the matrix, the interaction between the complex and the particular ligand is facilitated. Suitably, the surfactant is added and the resulting solution maintained for a period of time in the range of from 15 min up to 10 h, preferably from 30 min up to 4 h, before being contacted with the matrix.

It is a prerequisite in the first embodiment and preferred in the second embodiment, that the elution buffer contains a surfactant, suitably an anionic one such as sodium dodecyl sulfate (SDS). The surfactant enhances the effect of the compound comprising two or three nitrogen atoms bonded to a carbon atom, probably by uncovering the strong complex between endotoxins and ApoA, and subsequently separating the endotoxins from ApoA. The separation is most probably controlled by reaction kinetics, for which reason the period of time before equilibrium is reached can be substantial.

Examples of surfactants which can be used to advantage in the present invention are various bile acids or salts thereof, such as sodium deoxycholate and sodium cholate. Also, non-ionic surfactants, e.g. zero-net-charge surfactants such as polyoxyethylene sorbitan fatty esters, block co-polymers and alkyl ethoxylates, can be used to advantage in the present invention. Examples of polyoxyethylene sorbitan fatty esters are polyoxy-ethylene-(20)-sorbitan monolaurate, e.g. TWEEN® 80, and polyoxy-ethylene-(20)-sorbitan monooleate, e.g. TWEEN® 20, both sold by ICI of Great Britain. Examples of the block co-polymers are combinations of polypropyleneglycol and polyethyleneglycol, e.g. PLURONIC® sold by BASF in Germany. Examples of alkyl ethoxylates are TRITON® X-100 and TRITON® X-114 sold by Union Carbide in USA.

In the present invention, surfactant also includes various lipids, which can be natural or synthetic compounds consisting of acyl carriers, such as glycerides, sphingosine, cholesterol, or derivatives or mixtures thereof, to which one or more fatty acids can be bonded. The lipids can, depending on their polarity, be divided into non-polar, polar and amphiphilic lipids. Examples of non-polar lipids are monoacylglycerides, diacylglycerides, triacylglycerides, and cholesterol. Examples of polar and amphiphilic lipids are phospholipids and glycolipids. Suitably, the polar and amphiphilic lipids are bilayer forming, such as phosphatidylcholine (PC), phosphatidylinositol (PI), phosphatidylglycerol, phosphatidyletanolamine, phosphatidylserine, sphingomyelin, or mixtures thereof. The natural lipids can be produced from e.g. soybean oil, maize oil, soy lecithin and egg lecithin. Other suitable examples are synthetic and-saturated or unsaturated PC:s, such as dipalmitoyl phosphatidylcholine (DPPC) and dimyristyl phosphatidylcholine (DMPC).

The concentration of surfactant in the elution buffer can be in the range of from about 2 mM up to about 200 mM, suitably from 10 mM up to 100 mM. The concentration of surfactant is preferably in the range of from 15 mM up to 50 mM.

The pH of the elution buffer is suitably in the range of from about 5 up to about 9, and preferably in the range of from 6 up to 8.

The total ionic strength of the elution buffer can be in the range of from about 0.1 up to 20 mS/cm, suitably from 1 up to 8 mS/cm, and preferably from 2 up to 5 mS/cm.

The equilibration buffer, pretreatment buffer, sample washing buffer and the elution buffer can be the same or different. The concentration of surfactant, pH and total ionic strength can be the same or different than the values given for the elution buffer.

The process can be continuous, e.g. performed on a column, or batch-wise.

It is advantageous when carrying out the present invention to make use of a high temperature, since a high temperature more readily uncovers the strong complex between endotoxins and ApoA. The temperature is, however, limited to the range where irreversable denaturation of the protein does not occur. Thus, the temperature when carrying out the present invention, can be in the range of from about 2 up to about 95° C., suitably from 15 up to 90° C., preferably from 30 up to 85° C., more preferably from 40 up to 75° C.

The following examples are intended to further illustrate the present invention, without limiting the scope of said invention.

Experimental

Materials

Partly purified ApoA-IM in 20 mM Phosphate buffer, pH=7 was used as starting material in all performed tests. It was produced in *E. coli* by Pharmacia AB in Stockholm, Sweden.

The separation tests were carried out on various gels. Gel here denotes a matrix with immobilized compounds coupled thereto. Thus, tests were carried out on Arginine SEPHAROSE® 4B gel and an anion-exchange gel, Q SEPHAROSE® FF gel, both sold by Pharmacia Biotech of Uppsala, Sweden. Tests were also performed on PROSEP® Remtox gel sold by Bioprocessing Ltd. of Great Britain, and on a N66 POSIDYNE™ charged filter with filter disc, sold by Pall of Great Britain.

The analytical tests were carried out with Coatest Endotoxin and Endo-LAL, both of which are sold by Chromogeix of Mölndal, Sweden.

Analytical Methods

The quantity of ApoA-IM was determined using RP-HPLC. The method is used to identify ApoA-IM in the chromatograms and calculate the yield in the different methods. The relative standard deviation (RSD) of the method is 11%

UV-spectrophotometry was used for detection of protein in the chromatographic methods. The absorbance was measured at 280 nm.

The Limulus amebocyte lysat test (LAL test) is a specific method for measuring the concentration of endotoxins. The test is based on the primitive blood clotting mechanism in the horseshoe crab, *Limulus polyphemus*. The results are given in the unit EU, being equivalent to 0.1 ng of an average of various endo-toxins.

The gel clot endpoint test, also known as Endo-LAL is sold by Chromogenix of Mölndal, Sweden. In this test, an equal volume of LAL reagent (prepared from lysed limulus amebocyte cells) and test solution are mixed and incubated at 37° C. for one hour.

The chromogenic substrate test, also known as Coatest Endotoxin and sold by Chromogenix of Mölndal, Sweden, is a relatively new, quantitative procedure that is performed on a microtiter plate and read by spectrophotometry at 405 nm. This method contains the specific enzymes which are activated in the presence of endotoxins. The activated enzymes split off para-ritro aniline (pNA) from a synthetic substrate. The released pNA form a yellow color which is proportional to the amount of endotoxins present in the reaction mixture. A standard curve is performed and the amounts of endotoxins are read off. The color development is stopped by adding acetic acid. The method is reported to give a relative standard deviation (RSD) of 25%.

EXAMPLES

Example 1

Tests 1a to 1g (gels)

Five tests were performed on Arginine SEPHAROSE® (tests 1a to 1e) according to the invention. For comparison, one test was performed on Arginine SEPHAROSE® using a buffer withpout surfactant (test 1f). For further comparison using an elution buffer with surfactant, one test was performed on PROSEP® Remtox (test 1g) and two on POSIDYNE™ charged filters (1h to 1i).

To achieve comparable results between the various methods, tests 1a to 1g were performed in a similar way, each in one cycle. However, PROSEP® Remtox does not withstand treatment with 0.5 M NaOH. Therefore, the sanitation programmed in test 1g constitutes a modified program, where the concentration of NaOH is 0.1 M.

All tests were performed at room temperature (about 20° C.).

Packing flow rate: 1 ml/min.

Bed height: 7.5 to 9.5 cm

Gel volume: 6 to 7 ml

Equilibration Mode

Equilibration buffer (buffer 1): 0.1 M Tris-HCl+about 20 mM sodium deoxycholate, pH=8

Flow rate in equilibration: 0.5 ml/min

Total buffer volume: 5 column volumes

Sample treatment: about 20 mM sodium deoxycholate was added to the sample and the solution was mixed 30 min prior to loading onto the column.

Loading Mode

Sample loading: about 1 mg of ApoA-IM/ml gel

Flow rate: 0.2 ml/min

Elution Mode

Elution buffer (buffer 1): 0.1 M Tris-HCl+about 20 mM sodium deoxycholate, pH=8

Flow rate in elution: 0.2 ml/min

Sanitation Mode

After elution, the Arginine SEPHAROSE® and PROSEP® Remtox gels were washed with 4.5 column volumes of a first washing liquid containing 50% $C_2H_5OH$ and 5% HAc, followed by 4.5 column volumes of a second washing liquid containing 0.5 M NaOH (tests 1a to 1g). The washing was carried out three times.

Tests 1h to 1i (Charged Filters)

Two tests were performed on POSIDYNE™ charged filters (tests 1h to 1i) for comparison with the process according to invention. The tests were carried out in one cycle each.

In the two tests the filters were placed in a filter disc, a pump was connected and air was removed from the system.

Equilibration Mode

Flow rate: 1 ml/min

Duration: 40 min

Equilibration buffer (buffer 1) in test 1h: 0.1M Tris-HCl, pH=8

Equilibration buffer (buffer 2) in test 1i: 0.1M Tris-HCl+about 20 mM sodium deoxycholate, pH=8

Sample treatment: 4 ml buffer 1 in test 1h and 4 ml buffer 2 in test 1i were added to the samples and the solutions were mixed 30 min prior to loading onto the filter system.

Loading Mode

Samples: 1.2 mg of ApoA-IM/ml of sample solution, total volume 1 ml

Loading: The samples were circulated in the filter system for 30 min, whereupon the product was collected.

The filters were thrown away after each test.

The endotoxin values were analyzed with the LAL chromogenic substrate method (tests 1a to 1i). The concentration of endotoxins before treatment according to the invention, was between $10^6$ and $10^7$ EU/mg in all tests.

The results are evident from the following Table.

TABLE I

On-step processes for reducing the concentration of endotoxins in ApoA.

| Test no. | Method | Recovery (%) | EU/mg in end product | Reduction (times) |
| --- | --- | --- | --- | --- |
| Average values from 1a–1e | Arginine SEPHA-ROSE ® with surfacant | 53 | 900 | $1 \times 10$ |
| 1f | Arginine SEPHA-ROSE ® without surfacant | 15 | $8 \times 10^3$ | $1 \times 10^3$ |
| 1g | PROSEP ® Remtox with surfacant | 63 | $1 \times 10^5$ | 1 |

TABLE I-continued

On-step processes for reducing the concentration of endotoxins in ApoA.

| Test no. | Method | Recovery (%) | EU/mg in end product | Reduction (times) |
| --- | --- | --- | --- | --- |
| 1h | POSIDYNE ™ charged filter without surfacant | 68 | $5 \times 10^5$ | 2 |
| 1i | POSIDYNE ™ charged filter with surfacant | 77 | $4 \times 10^4$ | 30 |

As is evident from the Table, the present process is efficient in reducing the concentration of endotoxins attached to an ApoA. As is also evident from the Table, the absence of a surfactant in the elution buffer gives poor recovery and a higher concentration of endotoxins in the end product.

Example 2

The conditions in tests 2a to 2d coincided with those of tests 1a to 1g of Example 1, except that the concentration of Tris-HCl was 20 mM. The flow rate was 10 cm/h. All tests were performed at room temperature (about 20° C.).

The concentration of endotoxins before treatment according to the invention, was between $10^6$ and $10^7$ EU/mg in all tests. The recovery was at least 90%.

The results are evident from the following Table.

TABLE II

On-step process according to the invention, where the endotoxin values were analyzed with the LAL gel clot endpoint method.

| Test no. | Loading mg/ml gel | Loading EU/ml gel | Gel volume (ml) | EU/mg in end product | Reduction (times) |
| --- | --- | --- | --- | --- | --- |
| 2a | 1.2 | $>10^6$; $<10^7$ | 26 | >50; <100 | $>2 \times 10^4$; $<10^5$ |
| 2b | 0.9 | $>10^5$; $<10^6$ | 40 | >5; <10 | $>2 \times 10^4$; $<10^5$ |
| 2c | 0.8 | $>10^6$; $<10^7$ | 40 | >10; <20 | $>1 \times 10^5$; $<10^6$ |
| 2d | 2 | $>2 \times 10^6$; $<2 \times 10^7$ | 373 | >3.3; <6.6 | $>3 \times 10^5$; $<2 \times 10^6$ |

As is evident from the Table, the first embodiment of the present process is efficient in reducing the concentration of endotoxins attached to an ApoA.

Example 3

Tests were performed on a Q SEPHAROSE® FF gel (tests 3a and 3b). The gel volume was about 0.37 l and the flow rate in all steps 36 cm/h. The flow was downwards in steps 1 to 6, while the flow was upwards in step 7.

Step 1. Sanitation Mode

Prior to preequilibration, the Q SEPHAROSE® gel was washed with 4 l of a washing liquid containing 1.0 M NaOH (solution 1).

Step 2. Preequilibration Mode a) Preequilibration buffer (buffer 2): 0.2 M $Na_2HPO_4 \times 12H_2O$, pH=8.0

Total buffer volume: 3 l b) Distilled water

Total water volume: 5 l c) The concentration of remaining endotoxins was measured according to the LAL gel dot endpoint test: <0.125 EU/ml Step 3. Equilibration Mode Equilibration buffer (buffer 3): 0.01 M $Na_2HPO_4 \times 12 H_2O$, 6 M urea, pH=8.0

Total buffer volume: 10 l

Step 4. Loading Mode

Total sample volume: 2.55 l

Step 5. Sample Washing Mode

Sample washing buffer (buffer 3): 0.01 M $Na_2HPO_4 \times 12 H_2O$, 6 M urea, pH=8.0

Total buffer volume: 0.5 l

Step 6. Elution Mode

Elution buffer (buffer 4): 0.01 M $Na_2HPO_4 \times 12 H_2O$, 0.1 M NaCl, 6 M urea, pH=8.0

Total buffer volume: 8 l

Elution with a linear gradient 0–100% (distilled water and buffer 4) in 200 min

Step 7. Regeneration Mode

Regeneration buffer (buffer 5): 2 M NaCl

Total buffer volume: 0.75 l

The results are evident from the following Table.

TABLE III

Anion-exchange gel (Q SEPHRASE® FF gel) used according the invention for reducing the concentration of endotoxins in ApoA.

| Test no. | Loading (mg/ml gel) | Recovery (%) | EU/mg in starting material | EU/mg in end product | Reduction (times) |
|---|---|---|---|---|---|
| 3a | 1.4 | 77 | $2.4 \times 10$ | <1.3 | $1.9 \times 10^3$ |
| 3b | 2.8 | 46 | 43 | <0.3 | $1.5 \times 10^2$ |

As is evident from the Table, the second embodiment of the present process is also efficient in reducing the concentration of endotoxins attached to an ApoA.

Example 4

One test was performed on an Arginine SEPHAROSE® gel (test 4a) according to the invention, in two cycles. Another test was performed on a Q SEPHAROSE® FF gel (step 1) followed by an Arginine SEPHAROSE® gel (step 2) (test 4b) also according to the invention. The conditions in tests 4a and 4b coincided with those of Examples 1 and 3, as appropriate. All tests were performed at room temperature (about 20° C.).

The results are evident from the following Tables.

TABLE IV

Process with two consecutive Arginine SEPHAROSE® steps, and a process with an initial anion-exchange step followed by an Arginine SEPHAROSE®, both according to the invention. The endotoxin values given in Tables IV to VI were analyzed with the LAL gel clot endpoint method.

| Test no. | Method Step 1 | Method Step 2 | Total recovery (%) | EU/mg in end product | Reduction (times) |
|---|---|---|---|---|---|
| 4a | Arg.-Seph. | Arg.-Seph. | 81 | <14 | $4 \times 10^6$ |
| 4b | Anion-exchange | Arg.-Seph. | 76 | <8 | $10^6$ |

TABLE V

| | Step 1 | | | |
|---|---|---|---|---|
| Test no. | EU/mg in starting material | Recovery (%) | EU/mg in end product | Reduction (times) |
| 4a | $>10^6$; $<10^7$ | 87 | $>10^3$; $<2 \times 10^3$ | $>2 \times 10^3$; $< 9.5 \times 10^3$ |
| 4b | $>10^6$; $<10^7$ | 84 | >90, <180 | $>10^4$; $<6 \times 10^4$ |

TABLE VI[<]thead

| | Step 2 | |
|---|---|---|
| Test no. | Recovery (%) | Reduction (times) |
| 4a | 93 | >150 |
| 4b | 90 | >10 |

As is evident from the Tables, a two-step process according to the invention provides a means to reduce the concentration of endotoxins attached to an ApoA to very low levels.

Example 5

Tests 5a and 5b (With Urea)

Tests were performed on a DEAE SEPHAROSE® FF gel (tests 5a and 5b). The gel volume was about 114 l, the column height 15 cm and the flow rate in all steps about 50 cm/h (test 5a). The gel volume was about 85 l, the column height 30 cm and the flow rate in all steps about 50 cm/h (test 5b). Tests 5a and 5b were performed at room temperature (about 20° C.).

Step 1. Sanitation Mode a) The DEAE SEPHAROSE® gel was washed with a washing liquid containing 1.0 M NaOH (solution 1).

b) Distilled water c) The concentration of remaining endotoxins was measured according to the LAL gel clot endpoint test: <0.125 EU/ml Step 2. Equilibration Mode Equilibration buffer (buffer 2): 0.03 M Tris, 8 M urea, 1 mM dithiothreitol (DTT), pH=7.5

Step 3. Loading Mode

Step 4. Sample Washing Mode

Sample washing buffer (buffer 2): 0.03 M Tris, 8 M urea, 1 mM dithiothreitol (DTT), pH=7.5

Step 5. Elution Mode

Elution buffer (buffer 3): 0.055 M Tris, 8 M urea, 1 mM dithiotlreitol (DTT), pH=7.5

Step 6. Regeneration Mode

Regeneration buffer (buffer 4): 2 M NaCl

Test 5c (Without Urea)

One test was performed without urea present, for comparison with the present invention. The remaining conditions and concentrations were identical with those of test 5a.

The results are evident from the following Table.

TABLE VII

Anion-exchange gel (DEAE SEPHAROSE ® FF gel) used according the invention for reducing the concentration of endotoXins in ApoA. The endotoxin values given in Table V were analyzed with the LAL gel clot endpoint method.

| Test no. | Loading (mg/ml gel) | Recovery (%) | EU/mg in starting material | EU/mg in end product | Reduction (times) |
|---|---|---|---|---|---|
| 5a | 3 | 37 | $10^8$ | 10 | $10^7$ |
| 5b | 3 | 54 | 108 | $2 \times 10^3$ | $5 \times 10^5$ |
| 5c | 3 | 0 | — | — | — |

As is evident from the Table, the second embodiment of the present process is efficient in reducing the concentration of endotoxins attached to an ApoA also on a large scale. In the absence of urea, the recovery of ApoA is undetectable, for which reason the concentration of endotoxins could not be measured either.

The eluate from the DEAE SEPHAROSE® FF gel in test 5b, was brought to a column containing 60 ml of DEAE SEPHAROSE® FF gel, the bed height being 30 cm. The column was equilibrated with the elution buffer (buffer 3) according to tests 5a and 5b. The sample was loaded and run straight through the column, being eluted with the elution buffer (buffer 3). The second step of test 5b was performed at room temperature (about 20° C.).

The results are evident from the following Table.

TABLE VIII

Process with two consecutive DEAE SEPHARASE ® steps, both according to the invention. The endotoxin values given in Table VI were analyzed with the LAL gel clot endpoint method.

| Test no. | Step 1 | Step 2 | Total recovery (%) | EU/mg in end product | Reduction (times) |
|---|---|---|---|---|---|
| 5b | Anion-exchange | Anion-exchange | 38 | <2 | $>5 \times 10^7$ |

TABLE IX

| | | | Step 2 | | |
|---|---|---|---|---|---|
| Test no. | Loading (mg/ml gel) | Recovery (%) | EU/mg in starting material | EU/mg in end product | Reduction (times) |
| 5b | 6 | 70 | $2 \times 10^3$ | <2 | $>10^3$ |

As is evident from the Tables, a two-step process according to the invention provides a means to reduce the concentration of endotoxins attached to an ApoA to very low levels.

We claim:

1. A medicament comprising Apolipoprotein A (APO A) or Apolipoprotein E (APO E), or variants or mixtures thereof, in a therapeutically effective amount for treatment of atherosclerosis or cardiovascular diseases, the APO A or APO E, or variants or mixtures thereof having been purified by a process comprising (a) contacting a first aqueous solution comprising the APO A or APO E and endotoxins with a matrix comprising an immobilized compound with an end group comprising two or three nitrogen atoms bonded to a carbon atom for attaching the endotoxins to the matrix, and (b) subsequently treating the matrix comprising the immobilized compound with a second aqueous solution comprising a surfactant for releasing the APO A or APO E while the endotoxins remain attached to the matrix.

2. A method for treatment of atherosclerosis or cardiovascular diseases, comprising administering to an individual a therapeutically effective amount of Apolipoprotein A (APO A) or Apolipoprotein E (APO E), or variants or mixtures thereof, the APO A or APO E, or variants or mixtures thereof, having been purified by a process comprising (a) contacting a first aqueous solution comprising the APO A or APO E and endotoxins with a matrix comprising an immobilized compound with an end group comprising two or three nitrogen atoms bonded to a carbon atom for attaching the endotoxins to the matrix, and (b) subsequently treating the matrix comprising the immobilized compound with a second aqueous solution comprising a surfactant for releasing the APO A or APO E while the endotoxins remain attached to the matrix.

3. A medicament comprising apolipoprotein A (ApoA) or apolipoprotein E (ApoE), or variants or mixtures thereof, in a therapeutically effective amount for treatment of atherosclerosis or cardiovascular diseases, the ApoA or ApoE, or variants or mixtures thereof having been purified by a process comprising (a) contacting a first aqueous solution comprising the ApoA or ApoE and endotoxins with an anion-exchange matrix for attaching the ApoA or the ApoE, respectively, to the matrix, (b) subsequently treating the anion-exchange matrix with a second aqueous solution comprising a compound comprising two or three nitrogen atoms bonded to a carbon atom for releasing the endotoxins while the ApoA or ApoE remains attached to the matrix, and (c) then releasing the ApoA or ApoE from the matrix.

4. A method for treatment of atherosclerosis or cardiovascular diseases, comprising administering to an individual a therapeutically effective amount of apolipoprotein A (ApoA) or apolipoprotein E (ApoE), or variants or mixtures thereof, the ApoA or ApoE, or variants or mixtures thereof, having been purified by a process comprising (a) contacting a first aqueous solution comprising the ApoA or ApoE and endotoxins with an anion-exchange matrix for attaching the ApoA or the ApoE to the matrix, (b) subsequently treating the anion-exchange matrix with a second aqueous solution comprising a compound comprising two or three nitrogen atoms bonded to a carbon atom for releasing the endotoxins while the ApoA or ApoE remains attached to the matrix, and (c) then releasing the ApoA or ApoE from the matrix.

* * * * *